United States Patent
Kim et al.

(10) Patent No.: US 9,109,225 B2
(45) Date of Patent: Aug. 18, 2015

(54) ENGINEERED TRANSPOSON FOR FACILE CONSTRUCTION OF A RANDOM PROTEIN DOMAIN INSERTION LIBRARY

(71) Applicant: Polytechnic Institute of New York University, Brooklyn, NY (US)

(72) Inventors: Jin Ryoun Kim, Jericho, NJ (US); Vandan K. Shah, Ozone Park, NY (US); Brennal Pierre, Brooklyn, NY (US)

(73) Assignee: New York University, New York, NY (US)

( * ) Notice: Subject to any disclaimer, the term of this patent is extended or adjusted under 35 U.S.C. 154(b) by 4 days.

(21) Appl. No.: 14/025,945

(22) Filed: Sep. 13, 2013

(65) Prior Publication Data

US 2014/0080738 A1    Mar. 20, 2014

Related U.S. Application Data

(60) Provisional application No. 61/701,047, filed on Sep. 14, 2012.

(51) Int. Cl.
*C12N 15/10*    (2006.01)

(52) U.S. Cl.
CPC .................................. *C12N 15/1082* (2013.01)

(58) Field of Classification Search
None
See application file for complete search history.

(56) References Cited

PUBLICATIONS

Hoeller et al. (Journal of Microbiological Methods 75 (2008) 251-257).*
Haapa et al. (Nucleic Acids Research, 1999, vol. 27, No. 13 2777-2784).*
Yang et al.( Appl. Environ. Microbiol. 1989, 55(3):568).*

* cited by examiner

*Primary Examiner* — Christopher M Babic
*Assistant Examiner* — Sahana Kaup
(74) *Attorney, Agent, or Firm* — Laurence P. Colton; Smith Risley Tempel Santos LLC

(57) ABSTRACT

Methods for facile construction of a random domain insertion library (1) with optimal control of composition and length of inter-domain linker residues and (2) mediated by sticky-end ligation between host and guest DNA fragments. To develop such a method, we engineered a Mu transposon. The method exploits transposition of the engineered Mu transposon, which, upon removal, allows for sticky-end ligation between host and guest DNA fragments. We used a gene coding for xylanase from *bacillus circulans* (BCX) as a guest DNA sequence and the plasmid PUC19 containing lacZα as the target for insertion (i.e., a host DNA sequence). Results demonstrate that the method enables facile construction of a random domain insertion library with optimal control of composition and length of inter-domain linker residues.

14 Claims, 6 Drawing Sheets

Mu Transposon

MuST Transposon

SEQUENCE LISTING

```
<160> NUMBER OF SEQ ID NOS: 33

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
cgcactgatc aagcc                                                     15

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tggaccggtt cacgcaca                                                  18

<210> SEQ ID NO 3
<211> LENGTH: 15
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 3
acagatgatc aagcc                                                    15

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tggaccggtt caacagat                                                 18

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ggggatgatc aagcc                                                    15

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
tggaccggtt cagggat                                                  18

<210> SEQ ID NO 7
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ctgtgtgatc aagcc                                                    15

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tggaccggtt cactgtgt                                                 18

<210> SEQ ID NO 9
<211> LENGTH: 15
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 9
ctgggtgatc aagcc                                                15

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
tggaccggtt cactgggg                                             18

<210> SEQ ID NO 11
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
agccctgatc aagcc                                                15

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tggaccggtt caagcccg                                             18

<210> SEQ ID NO 13
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
catattgatc aagcc                                                15

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
tggaccggtt cacatatg                                             18

<210> SEQ ID NO 15
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
ccatttgatc aagcc                                                        15

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tggaccggtt caccattc                                                     18

<210> SEQ ID NO 17
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
cggtgtgatc aagcc                                                        15

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
tggaccggtt cacggtgc                                                     18

<210> SEQ ID NO 19
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
ctgtgtgatc aagcc                                                        15

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
tggaccggtt cactgtgt                                                     18

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tgatcaggcg cacgaaaaac gcgaa                                           25

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tgcgaaagcg caaaaagcac gtggccaagt                                      30

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tgtgaaatac cgcacagatg atca                                            24

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tggccaagtt gtctacgca                                                  19

<210> SEQ ID NO 25
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
tgatcaagcc                                                            10

<210> SEQ ID NO 26
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(12)

<400> SEQUENCE: 26 tgg acc ggt tca                                                       12
Trp Thr Gly Ser
1

<210> SEQ ID NO 27
<211> LENGTH: 4
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 27

Trp Thr Gly Ser
1

<210> SEQ ID NO 28
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
tgtgaaatac cgcacagatg atcaggcgc                                            29

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
cgtgcaccgg ttcaacagat gcgt                                                 24

<210> SEQ ID NO 30
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
tgatcaggcg c                                                               11

<210> SEQ ID NO 31
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
cgtgcaccgg ttca                                                            14

<210> SEQ ID NO 32
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
tgaagcggcg c                                                               11

<210> SEQ ID NO 33
<211> LENGTH: 14
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 33
cgtgcgccgc ttca                                                          14
```

ENGINEERED TRANSPOSON FOR FACILE CONSTRUCTION OF A RANDOM PROTEIN DOMAIN INSERTION LIBRARY

STATEMENT OF RELATED APPLICATIONS

This application is a non-provisional of and claims the benefit of U.S. Provisional Patent Application No. 61/701,047 having a filing date of 14 Sep. 2012.

SEQUENCE LISTING

The instant application contains a Sequence Listing which has been submitted in ASCII format via EFS-Web and is hereby incorporated by reference in its entirety. Said ASCII copy, created on Oct. 17, 2013, is named 48467.051U1_SL.txt and is 8,212 bytes in size.

BACKGROUND OF THE INVENTION

1. Technical Field

The present invention is generally related to the field of methods for construction of random domain insertion libraries, and more specifically related to the field of methods for construction of a random insertion library with optimal control of composition and length of inter-domain linker residues and mediated by sticky-end ligation between host and guest DNA fragments.

2. Prior Art

The ability to create fusion proteins by connecting two or more protein domains is advantageous in protein engineering because it can introduce a wide range of novel and integrated functions. A mode of protein fusion which has been most extensively used and studied is end-to-end fusion [1-2]. In this method, the N-terminus of one protein is fused to the C-terminus of the other protein. While end-to-end fusion has successfully been used to create multi-functional, multi-domain proteins, insertional fusion has recently been recognized as a novel tool to produce integrated and coupled functionalities through inter-domain interactions [3-9].

In insertional fusion, a guest protein is inserted into the middle of a host protein through multiple tethers connecting the two protein domains [3-9]. Insertional fusion has resulted in creation of allosteric protein switches [3-5,7,9] and stabilization of a guest protein domain [6,8]. The close proximity of the N- and C-termini of a guest protein seems to increase the chance of successful insertion. Nearly 50% of single-domain proteins have their N- and C-termini proximal [10], indicating the potential application of insertional fusion to a wide range of proteins. Proteins whose two termini are more distal can also be functionally inserted with the introduction of appropriate linkers [11].

One of the most important factors to consider in insertional fusion is selection of insertion sites, which may determine inter-domain interactions. For insertion sites, loops of a host protein have been extensively used because these locations are usually tolerant of insertion of a large guest protein domain [6,8,12,13]. Insertion sites may also be rationally selected with the aid from computational structure modeling on protein insertion complexes [14,15]. However, there is no robust guideline for selection of insertion sites ensuring the desired functional outcome of insertional fusion. Moreover, construction of a protein insertion complex is usually time-consuming and, as such, testing of multiple insertion sites one by one is not always highly efficient. More comprehensive and systematic examination of insertion sites is possible through construction of random insertion libraries followed by high throughput evaluation of these libraries for functional outcomes [3,16,17]. In this combinatorial approach, a guest protein domain is randomly inserted into a host protein domain.

Characteristics of linker residues joining the fused protein domains can also play an important role in inter-domain interactions [3,16,18,19]. In protein fusion complexes, linkers are introduced to alleviate any steric conflicts between protein domains [20,21]. Relatively small and hydrophilic residues are usually preferred as inter-domain linker residues [3,22] as inclusion of these linker residues are likely to maintain structures and functions of the fused protein domains [19,22]. The amino acids preferentially found in naturally occurring inter-domain linkers include Arg, Asn, Asp, Gln, Glu, Gly, Lys, Pro, Ser and Thr [20,22]. As most inter-domain linkers are likely to be solvent-exposed, inclusion of bulky hydrophobic residues might be energetically destabilizing and/or cause undesired intramolecular or intermolecular hydrophobic interactions [22]. Flexible inter-domain linker residues such as Asp, Gly, Lys and Ser have been widely used for construction of engineered protein insertion complexes [3,6,7,16] and are effective in control of functional dynamics of domains [19]. It was found that composition rather than amino acid sequence of a linker determines linker flexibility [21]. Inclusion of multiple cysteine residues in linkers is undesired under most circumstances due to possible formation of unwanted disulfide bonds.

The presence of too short inter-domain linkers should be avoided in insertional fusion because of potential structural conflicts between the fused domains [3]. Inclusion of too long inter-domain linkers is also not preferred as the chance of inter-domain interactions, which are critical in functional integration of protein domains in insertional fusion, may be significantly reduced in this case [3]. The inter-domain linker length may also determine stability of a fusion protein [18,21]. The average length of naturally occurring inter-domain linkers corresponds to ~5-6 residues [19,22,23]. Similarly, inclusion of 3-5 residue inter-domain linkers was found to be effective at conserving structures and functions of the fused domains in engineered protein insertion complexes [3,6,24]. Taken altogether, optimal control of amino acid composition and length of an inter-domain linker would be highly beneficial in constructing random insertion libraries with a high likelihood of functional integration of the fused domains.

In combinatorial engineering for protein insertional fusion, DNaseI is commonly used to randomly introduce single cuts in plasmids harboring a DNA sequence encoding a host protein [16,17,25]. After DNaseI digestion, the resultant overhang strands created within single cut linear plasmids are repaired by DNA polymerase to prepare blunt ends. The repaired linear plasmids are then blunt end-ligated with DNA encoding a guest protein. Unfortunately, generation of single cuts in target DNA using DNaseI is not always straightforward and instead requires the delicate control of DNaseI activities, which is often difficult to achieve [26]. Alternatively, one may use S1 nuclease to overcome this difficulty [26]. However, the nonspecific nuclease (e.g., DNaseI and S1 nuclease)-mediated DNA digestion results in occurrence of uncontrolled tandem duplication and/or deletion of a host DNA sequence on ends of an inserted guest DNA sequence [17,26,27]. While such tandem duplication and/or deletion may provide additional diversity in a library in terms of the distance between the two fused domains [17,27], control of amino acid composition and length of linkers is difficult in this case. DNA digestion for random insertion can also be made chemically [28] but this procedure is complicated and was found to generate unwanted mutations [28].

As an alternative, one may consider using a transposon, a DNA element that can be randomly inserted into a host DNA sequence with a high efficiency and accuracy [29], for construction of random domain insertion libraries [30]. Transposons are able to translocate to a variety of sites on DNA of any host organism [31]. Among many transposons, a bacteriophage Mu transposon has been extensively studied [29] and, because of its low target site preference [29], used to construct random domain insertion libraries [3]. The Mu transposon has a 22 bp symmetrical consensus sequence, located near both ends, for recognition by MuA transposase [31-32]. Random transposition of a Mu transposon into a target gene occur through (1) binding of MuA transposase monomers to the Mu transposon recognition sites to form transposome assemblies [31], (2) tetramerization of the bound MuA transposase monomers to bridge the ends of the Mu transposon and engage the Mu transposon cleavage sites (i.e., sequences containing (T or A)CA↓ located at 5 bps beyond the terminal recognition sites [33-34], (3) subsequent self-cleavage of the Mu transposon at the cleavage sites [35], and (4) accurate occurrence of a 5 bp staggered cut in a host DNA sequence into which the Mu transposon is subsequently incorporated [29,34,36,37].

High fidelity of the transposition mechanism results in precise 5 bp duplication of a host DNA sequence occurring upon transposition of the Mu transposon [29,31,36,37]. This is in contrast with the aforementioned uncontrolled occurrence of tandem nucleotide duplication and/or deletion found in random domain insertion mediated by nonspecific nucleases [17,26,27]. A gene of interest (i.e., a guest DNA sequence) may be included in a transposon along with other genetic components required for random transposition. However, direct application of a transposon in this manner is not optimal for control of inter-domain linker residues in random insertion libraries [38]. This is because necessary transposon components flanking a guest DNA sequence remain in the host DNA sequence after transposition, and encode suboptimal inter-domain linkers [9,38-40].

Control of inter-domain linker residues was previously found to be possible by removal of randomly inserted whole transposon elements from a host DNA sequence, which is then re-ligated with a guest DNA sequence encoding a guest protein flanked by desired inter-domain linker residues [3]. However, similar to nonspecific nuclease-based methods, construction of random domain insertion libraries in this manner relies on blunt-end ligation between host and guest DNA fragments, which is much less efficient than sticky-end ligation [41-43], thus lowering library construction efficiency. Blunt-end ligation causes not only recircularization of a host DNA fragment without a guest DNA fragment being inserted, but also inclusion of multiple guest DNA copies, decreasing library quality [3]. Moreover, the restriction enzyme site used in this previous study to remove randomly inserted transposons while causing minimal nucleotide deletion in a host DNA sequence is relatively abundant, limiting application of this method for other host DNA sequences [3].

Therefore, there is a need for an engineered transposon for facile construction of a random protein domain insertion library. It is to such a need and others that the present invention is directed.

BRIEF SUMMARY OF THE INVENTION

Insertional fusion between multiple protein domains represents a novel means of creating integrated functionalities. Currently, there is no robust guideline for selection of insertion sites ensuring the desired functional outcome of insertional fusion. Therefore, construction and testing of random domain insertion libraries, where a host protein domain is randomly inserted into a guest protein domain, significantly benefit extensive exploration of sequence spaces for insertion sites. Short peptide residues are usually introduced between protein domains to alleviate structural conflicts and the inter-domain linker residues may affect the functional outcome of protein insertion complexes. Unfortunately, optimal control of inter-domain linker residues is not always available in conventional methods used to construct random domain insertion libraries. Moreover, most conventional methods employ blunt-end rather than sticky-end ligation between host and guest DNA fragments, thus lowering library construction efficiency.

Briefly, the present invention provides for the facile construction of random domain insertion libraries using an engineered transposon. We show that random domain insertion with optimal control of inter-domain linker residues is possible with our engineered transposon-based method. In addition, our method employs sticky-end rather than blunt-end ligation between host and guest DNA fragments, thus allowing for facile construction of relatively large size libraries.

In the present invention, we describe the development of a useful alternative to conventional methods for facile construction of a random domain insertion library. In one embodiment, we are particularly interested in construction of a random insertion library (1) with optimal control of composition and length of inter-domain linker residues and (2) mediated by sticky-end ligation between host and guest DNA fragments. To develop such a method, we sought to engineer a Mu transposon. As our method exploits transposition of the engineered Mu transposon, which, upon removal, allows for sticky-end ligation between host and guest DNA fragments, we refer to this engineered transposon as the MuST transposon. In this invention, we use a gene coding for xylanase from *bacillus circulans* (BCX) as a guest DNA sequence and the plasmid PUC19 containing lacZα as the target for insertion (i.e., a host DNA sequence). Results presented here demonstrate that our method enables facile construction of a random domain insertion library with optimal control of composition and length of inter-domain linker residues.

In summary, results from our study presented here demonstrate the high promise of using the engineered MuST transposon for construction of random protein domain insertion libraries through sticky-end ligation between host and guest DNA fragments. We provide evidence that our method allowed for optimal control of inter-domain linker residues. As such, our MuST transposon-based method represents a valuable, complementary tool for facile construction of random domain insertion libraries.

These features, and other features and advantages of the present invention, will become more apparent to those of ordinary skill in the relevant art when the following detailed description of the preferred embodiments is read in conjunction with the appended figures.

BRIEF DESCRIPTION OF THE FIGURES

FIG. 1B discloses the nucleotide sequences as SEQ ID NOS 25-26, respectively, in order of appearance, and the protein sequence as SEQ ID NO: 27.

FIG. 2 discloses SEQ ID NOS 28-31 and 25-26, respectively, in order of appearance.

FIG. 6 discloses SEQ ID NOS 32-33 and 28-29, respectively, in order of appearance.

DETAILED DESCRIPTION OF PREFERRED EMBODIMENTS

Genetic Components Included in the MuST Transposon.

We created the engineered MuST transposon by including unique restriction enzyme sites at the 5' and 3' ends of the Mu transposon to enable optimization of inter-domain linker residues as well as sticky-end ligation between a host DNA fragment (i.e. bcx) and a guest DNA fragment (i.e., PUC19). For efficient selection of clones containing the randomly inserted MuST transposon, the chloramphenicol resistant (CmR) gene and other genetic components necessary for expression of this gene was included in the MuST transposon. The host plasmid PUC19 displays the ampicillin resistance (AmpR) but lacks CmR and, as such, only clones containing the MuST transposon inserted into PUC19 should be able to grow on Amp/Cm plates.

Figure 1:
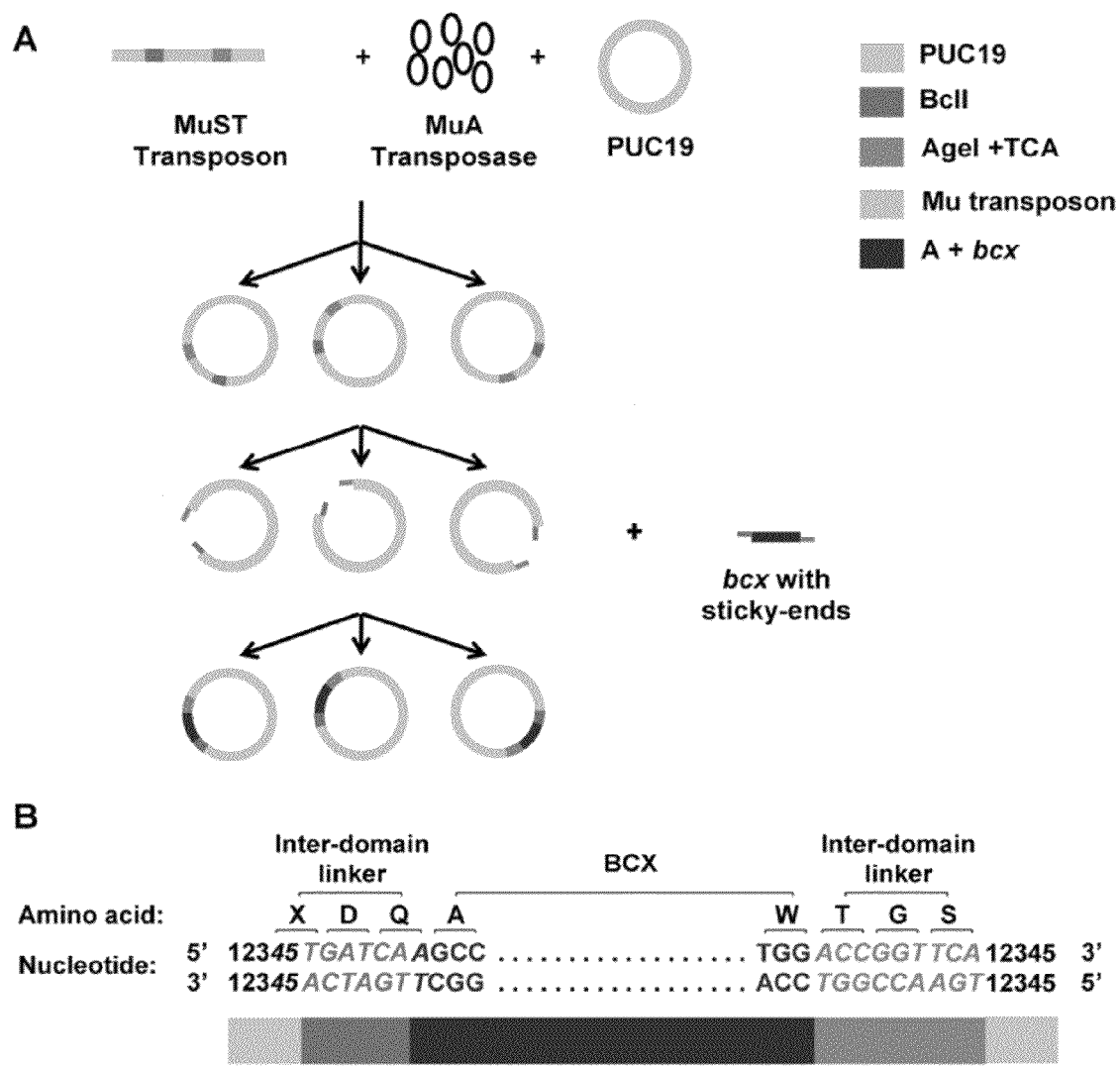
FIG. 1 shows (A) a schematic of random insertion of bcx into PUC19 containing lacZα, and (B) a sequence schematic of bcx randomly inserted into PUC19.
Figure 2:
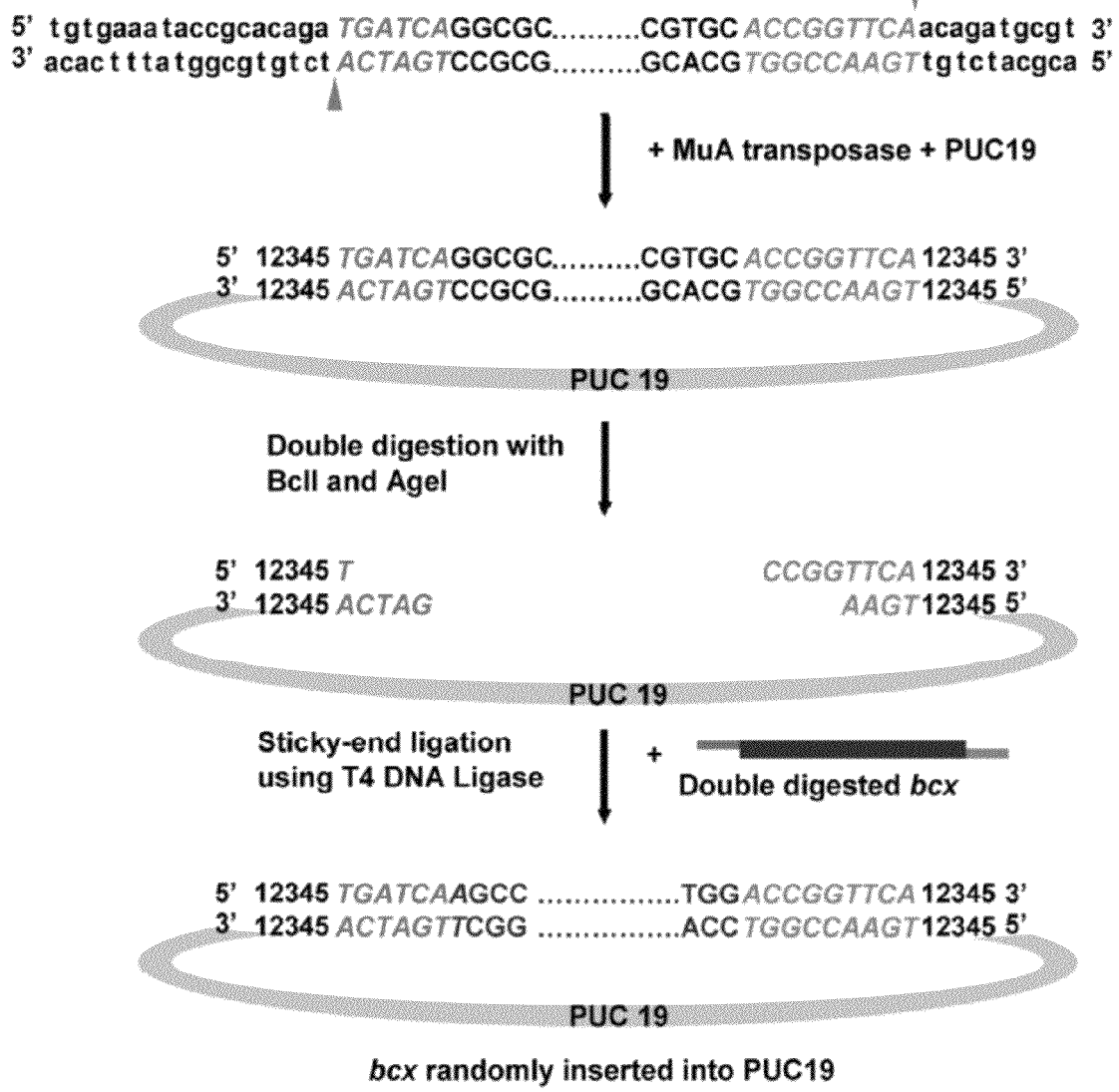
FIG. 2 shows a detailed schematic of random insertion of bcx into PUC19 containing lacZα shown along with nucleotide sequence changes occurring after individual steps.

A schematic of construction of random domain insertion libraries using the MuST transposon is shown in FIGS. 1A and 2. Briefly, random transposition of the MuST transposon into the host plasmid PUC19 was allowed to occur in vitro. The whole MuST transposon was then removed from the plasmid by restriction enzyme digestion. This restriction enzyme digestion resulted in production of random single cut plasmids, which were then sticky-end ligated with a guest DNA fragment (i.e., bcx).

FIG. 1 shows (A) A schematic of random insertion of bcx into PUC19 containing lacZα. Random transposition of the MuST transposon into the host plasmid PUC19 is mediated by MuA transposase. After random transposition, the MuST transposon is removed by double digestion using BclI and AgeI restriction enzymes. The double digested PUC19 is then sticky-end ligated with a guest DNA fragment containing bcx. Additional 5' adenine is contained at the upstream of bcx for in-frame connection between BCX and desired inter-domain linker residues. (B) A sequence schematic of bcx randomly inserted into PUC19. The BclI (TGATCA) site is shown in green. The AgeI (ACCGGT)+TCA site is shown in red. Numbers (i.e., 12345) represent nucleotide sequences derived from PUC19. Nucleotide sequences encoding linkers (i.e., 45TGATCAA and ACCGGTTCA) are shown in italic. The first and last codons of BCX (i.e., GCC and TGG, respectively) are shown in plain font. X represents one of fifteen amino acids (i.e., Ala, Arg, Asn, Asp, Cys, Gly, His, Ile, Leu, Phe, Pro, Ser (twice), Thr, Tyr and Val) encoded by a codon containing 3' thymine. Colored blocks shown below indicate the followings; gray for nucleotide sequences derived from PUC19, green for the BclI site, dark blue for additional 5' adenine+bcx, and red for the AgeI+TCA site.

FIG. 2 shows a detailed schematic of random insertion of bcx into PUC19 containing lacZα shown along with nucleotide sequence changes occurring after individual steps. The MuST transposon shown on the top contains nucleotide sequences derived from PUC19 (shown in black lowercase letters), the BclI site (shown in green italic uppercase letters), the AgeI+TCA site (shown in red italic uppercase letters). Other nucleotide sequences necessary for random transposition of the MuST transposon are shown in black plain uppercase letters. The cleavage sites (i.e., (T or A)CA↓) are shown with arrowheads. Random transposition of the MuST transposon into the host plasmid PUC19 occurs in the presence of MuA transposase. Double digestion of the resulting plasmids using BclI and AgeI creates overhangs for sticky-end ligation with bcx. Additional 5' adenine placed at the upstream of bcx ensures in-frame connection between BCX and desired inter-domain linker residues. Numbers (i.e., 12345) represent nucleotide sequences derived from PUC19.

Design of the Engineered MuST Transposon.

Figure 6:
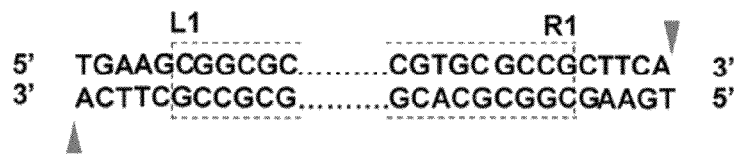
FIG. 6 shows a comparison of the Mu transposon and the MuST transposon.
Figure 6:

To introduce preferred types of amino acids in inter-domain linkers while keeping the inter-domain linker lengths at an optimal range, we mutated the Mu transposon to introduce the BclI site (TGATCA) and the AgeI site (ACCGGT) at its 5' and 3' ends, respectively (FIG. 6).

FIG. 6 shows a comparison of the Mu transposon and the MuST transposon. In the Mu transposon, L1 and R1 represent the outermost recognition sites for MuA transposase. In addition, the Mu transposon has the CmR gene, four additional recognition sites and other genetic components, all of which are not shown in FIG. 6. The Mu transposon used in the present invention was a pre-cleaved transposon where sequences outside of the cleavage sites (i.e., 5'-(T or A)CA↓ shown with arrowheads in FIG. 6) were previously removed. Several mutations were introduced to construct the MuST transposon from the Mu transposon and the mutated nucleotides are shown with underlines. In the MuST transposon, the BclI (TGATCA) and AgeI (ACCGGT)+TCA sites are shown in green italic and red italic, respectively. The cleavage sites are also shown with arrowheads in the MuST transposon. Nucleotide sequences derived from PUC19 are shown in lowercase letters.

To minimize undesired effects on transposition [44], most mutations to create the MuST transposon were made outside of Mu transposon regions involved in various transposition steps (e.g., cleavage sites and recognition sites for MuA transposase binding) [44]. For example, no mutation was introduced in the transposon cleavage sites (i.e., 5'-(T or A)CA↓ in FIG. 6), which were located 5 bp away from the terminal recognition sites L1 and R1 (FIG. 6). Only one nucleotide mutation each was made in the L1 and R1 sites of the Mu transposon (FIG. 6). The three additional nucleotide mutations were introduced outside of the cleavage site and the recognition sites (FIG. 6). Our preliminary experiments indicated that a transposition efficiency of the MuST transposon was modestly (~6-fold) reduced when compared with the wild-type Mu transposon (data not shown).

From all possible reading frames, we placed TGATCAA (i.e., BclI site+A) in the second reading frame where GATCAA codes for Asp-Gln as inter-domain linker residues fused to the N-terminus of a guest protein domain (FIG. 1B). On the other hand, we placed ACCGGTTCA (i.e., AgeI site+TCA) in the first frame where ACCGGTTCA encodes Thr-Gly-Ser as inter-domain linker residues fused to the C terminus of a guest protein domain (FIG. 1B). Note that these five amino acids (i.e., Asp, Gln, Gly, Ser and Thr) are those preferred as inter-domain linker residues [3,6,7,20,22], as described in the Brief Summary of the Invention. Though sequence uncertainty exists at one residue (i.e., that encoded by 45T in FIG. 1B) at the upstream of Asp-Gln, this uncertainty is unlikely to produce significantly negative outcomes; while XXT may code for fifteen different amino acids, a chance of encoding the aforementioned residues preferred for inter-domain linkers is relatively high (~½). Other than these linker residues, only one residue (i.e., that encoded by 123 in FIG. 1B) derived from the host protein domain was expected to be duplicated (FIG. 1B). The expected 5 bp duplication is an inherent feature of the Mu transposon [29,31,36,37].

Taken altogether, the described design of the MuST transposon would allow for optimal control of inter-domain linker residues in terms of number and amino acid composition. It should be noted that one may introduce additional inter-domain linker residues simply by genetic inclusion of necessary codons at the termini of a guest DNA sequence before ligation to a random single cut host DNA fragment. Other restriction enzyme sites in place of BclI and AgeI sites within the MuST transposon may also be used to incorporate other kinds of inter-domain linker residues. While out-of-frame fusion between host and guest DNA sequences may still occur in our method as was the case with other conventional methods [3,27], functional selection, if any, for a guest protein domain should enable isolation of clones containing the desired in-frame fusion [3,27].

Construction of the MuST Transposon Using PCR.

Figure 3:
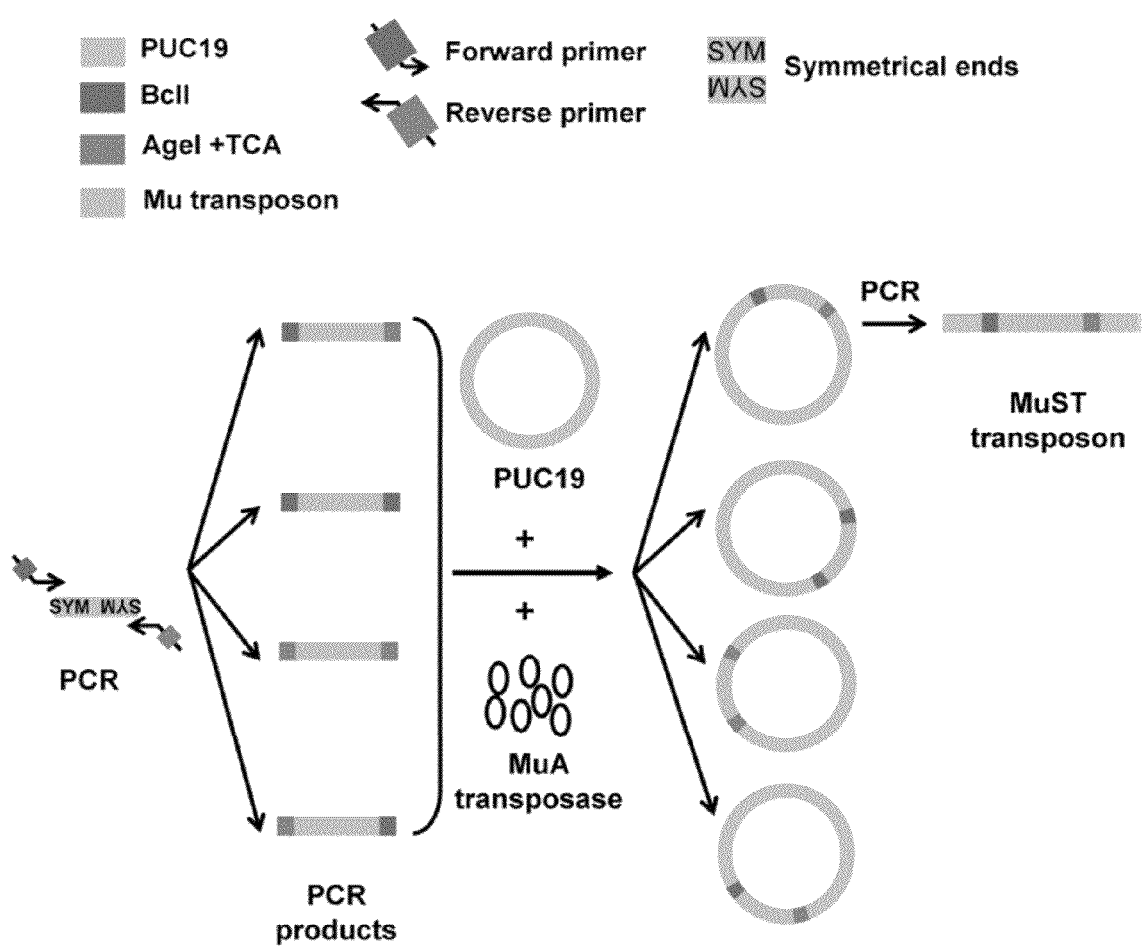
FIG. 3 shows an illustrative construction of the MuST transposon of the present invention.

As described earlier in the Brief Summary of the Invention, a Mu transposon has a 22 bp consensus recognition sequence at its termini, which are identical when read from 5' to 3' ends (FIG. 6). Due to the presence of identical sequences at the termini, the desired incorporation of two different restriction enzyme sites at the respective ends of the Mu transposon by PCR is not straightforward; in the annealing step during PCR, both forward and reverse primers can anneal at either end. PCR through this nonspecific annealing of primers can produce a mixture of the following four transposon mutants with sequence variation at the termini; AgeI+TCA sites on both ends, BclI sites on both ends, BclI at 5' and AgeI+TCA at 3' ends, and AgeI+TCA at 5' and BclI at 3' ends (FIG. 3). Our preliminary results from initial transposition of the transposon mutant mixture, which was directly obtained from PCR, indicated that ~25% of colonies displaying AmpR and CmR contained the desired MuST transposon sequence (i.e., BclI at 5' and AgeI+TCA at 3' ends) inserted into PUC19.

FIG. 3 shows an illustrative construction of the MuST transposon of the present invention. The Mu transposon were genetically modified using PCR to introduce the BclI site at the 5' and the AgeI+TCA site at the 3' termini. Due to the presence of symmetrical sequences at the 5' and 3' termini of the Mu transposon, the following four Mu transposon mutants with sequence variation at the termini were produced after PCR: AgeI+TCA on both ends; BclI on both ends; BclI at 5' and AgeI+TCA at 3' ends; and AgeI+TCA at 5' and BclI at 3' ends. Random transposition of the Mu transposon mutant mixture into PUC19 was then carried out in the presence of MuA transposase. The plasmid with insertion of the desired MuST transposon sequence (i.e., BclI at 5' and AgeI+TCA at 3' ends) was selected, purified and then used as a template for the second PCR for amplification of the MuST transposon. As a result, the MuST transposon contained an additional 18 bp fragment at the upstream of BclI and 10 bp fragment at the downstream of AgeI+TCA sites. These additional DNA fragments were derived from PUC19.

The plasmid with insertion of the desired MuST transposon sequence was then purified and used as a template for the subsequent second PCR for amplification of the MuST transposon (FIG. 3). The resulting MuST transposon contained not only the desired restriction enzyme sites but also an additional 18 bp fragment at the upstream of BclI and 10 bp fragment at the downstream of AgeI+TCA sites (FIG. 6). These additional DNA fragments were derived from PUC19 and inclusion of these sequences was necessary for specific priming in the second PCR (FIG. 3).

Random Transposition of the MuST Transposon into PUC19.

Random transposition of the MuST transposon into PUC19 was then carried out with MuA transposase in vitro. The subsequent transformation of the transposition reaction mixture into DH5α followed by plating the cells on the Amp/Cm plates generated libraries with a transposition efficiency of ~5×10⁴ CFU/µg of DNA. Given the observed transformation efficiency of ~1×10⁹ CFU/µg of DNA for DH5α, this transposition efficiency indicated that ~0.005% of plasmids contained the inserted MuST transposons and thus displayed CmR. The preliminary sequencing results showed that single rather than multiple MuST transposon molecule was randomly inserted into PUC19 as desired (data not shown; see the text below for detailed characteristics of random insertion of bcx into PUC19).

Preparation of Linear Plasmids with Random Single Cuts.

We then sought to double digest the PUC19 plasmids with randomly inserted MuST transposons using BclI and AgeI to prepare linear plasmids with random single cuts ready for sticky-end ligation with bcx. These restriction enzyme sites were absent in the wild-type PUC19 and were derived from the MuST transposon. BclI digestion of the plasmids with randomly inserted MuST transposons directly obtained from DH5α was however impossible. This is because adenosine in GATC (i.e., a part of the BclI site) became methylated through replication of the plasmids in dam+ DH5α and such methylation inhibited digestion of the plasmids using the BclI restriction enzyme [45]. Instead, plasmids with randomly inserted MuST transposons isolated en masse from DH5α were retransformed into dam–/dcm– E. coli cells to prepare Dam methylation-free plasmids, which were readily digestible by the BclI restriction enzyme as desired (data not shown). After double digestion of the plasmids using AgeI and BclI, the resulting linear plasmids lacking the MuST transposon sequence were isolated and purified en masse. The size of random single cut PUC19 prepared in this manner was identical to that of the wild-type PUC19 (i.e., ~2700 bp) (data not shown), further confirming that random insertion into PUC19 occurred predominantly with single rather than multiple MuST transposon molecule.

Ligation of the bcx Gene with Random Single Cut Plasmids.

For sticky-end ligation with the random single cut PUC19 plasmids, BclI and AgeI sites were genetically appended to the 5' and 3' ends of bcx, respectively. The additional adenine placed at the upstream of the 5' end of bcx ensured that inter-domain linker residues, Asp-Gln, were fused in-frame to BCX (FIG. 1B). After digestion using BclI and AgeI, the resulting bcx gene was sticky-end ligated with the linear random single cut PUC19 plasmids. Subsequent transformation of the ligation mixture into DH5α followed by plating the cells on Amp plates produced ~5×10⁵ CFU/µg DNA.

Figure 4:
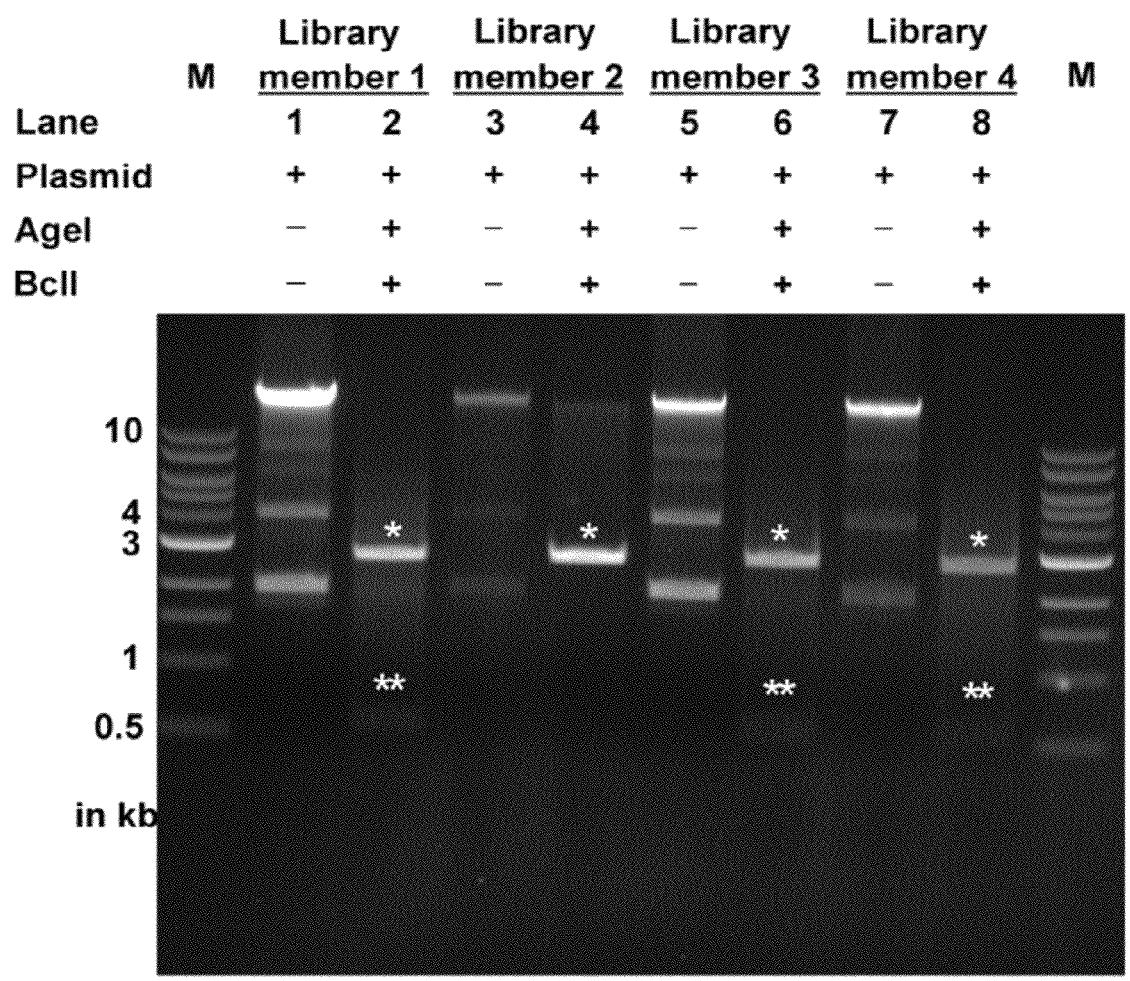
FIG. 4 shows Agarose gel electrophoresis analysis of plasmids obtained from randomly selected four library members generated by transformation of sticky-end ligation mixtures, which contained random single cut PUC19 and bcx, into DH5α cells.

FIG. 4 shows Agarose gel electrophoresis analysis of plasmids obtained from randomly selected four library members generated by transformation of sticky-end ligation mixtures, which contained random single cut PUC19 and bcx, into DH5α cells. Plasmids were run on 1% agarose gel before (for lanes 1, 3, 5 and 7) and after (for lanes 2, 4, 6 and 8) double digestion using AgeI and BclI. Results from four randomly selected library members are shown in FIG. 4. M represents molecular weight markers. *: linear PUC19. **: bcx.

A few colonies were randomly selected from the naïve library and plasmids were then obtained from these colonies. The plasmids were subsequently double digested using BclI and AgeI to examine characteristics of bcx insertion into PUC19 (FIG. 4). The presence of two bands corresponding to the sizes of PUC19 (i.e., ~2700 bp) and bcx (i.e., ~550 bp), respectively, was detected in agarose gel electrophoresis analysis of most library members, indicating that insertion occurred as desired (FIG. 4). Though the bcx gene was absent in some library members as judged by agarose gel electrophoresis analysis (see library member 2 in FIG. 4), results from similar double digestion of plasmids obtained from 26 randomly selected library members indicated that insertion of bcx into PUC19 occurred in most (~90%) transformants.

Figure 5:
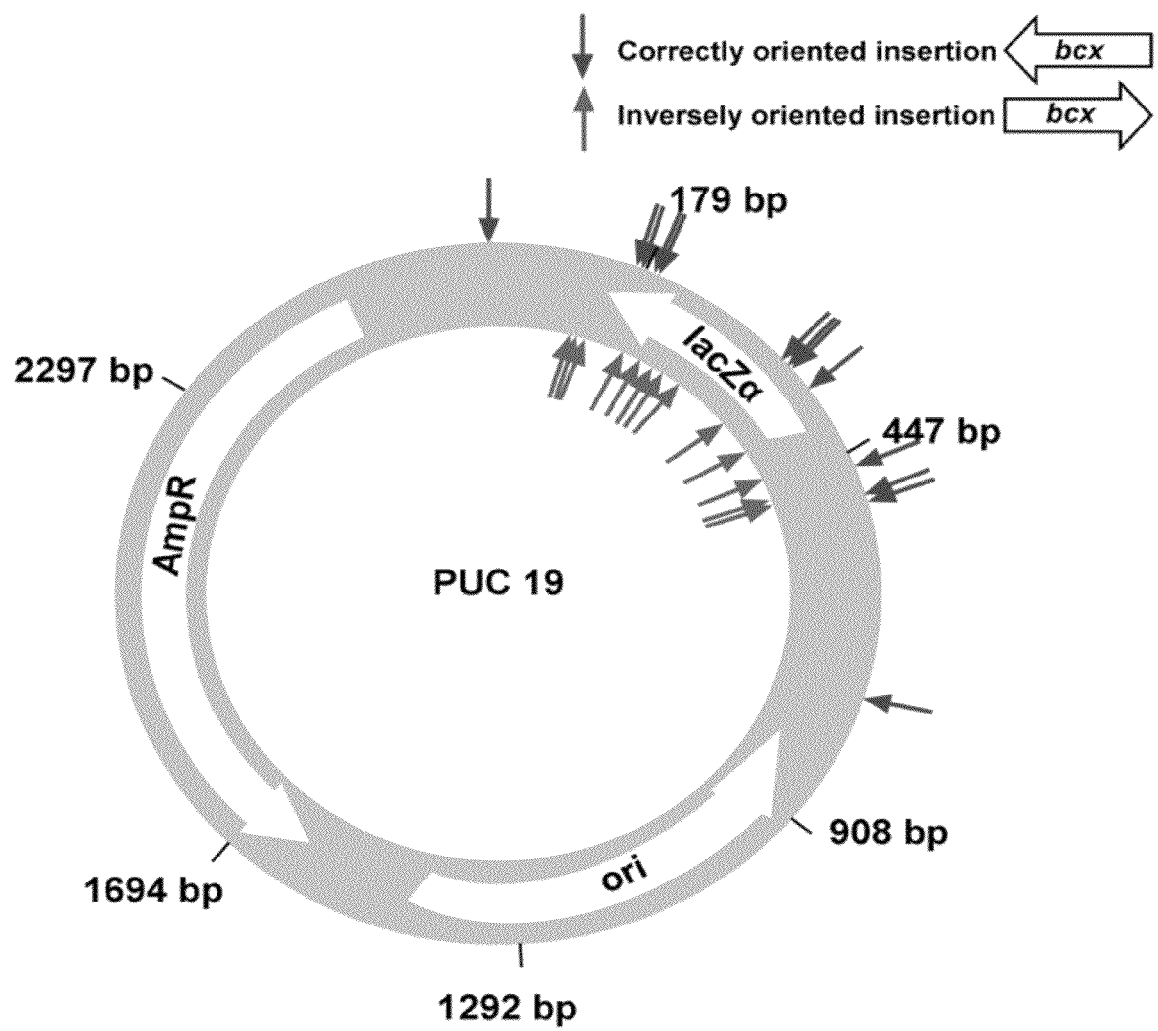
FIG. 5 shows positions of correctly oriented (red arrow) and inversely oriented (blue arrow) insertions of bcx into PUC19.

FIG. 5 shows positions of correctly oriented (red arrow) and inversely oriented (blue arrow) insertions of bcx into PUC19. Sequencing results of the 26 randomly selected library members indicated that insertion was suitably random (i.e., the 26 library members were unique at the genetic level) (FIG. 5). Most bcx insertion positions were distributed throughout lacZα and its neighboring regions (FIG. 5). No bcx insertion was detected in PUC19 regions responsible for AmpR and plasmid replication (FIG. 5) as was the case with other previous insertion studies [27,38] because these regions were crucial for the growth of library members in the presence of Amp.

The sequencing results also showed that bcx was inserted into PUC19 with correct orientation in the 13 randomly selected library members while inversely oriented insertion was also observed in the other 13 library members (FIG. 5), indicating that the ratio of having correctly oriented insertions to inversely oriented insertions was ~1:1. Note that colonies containing PUC19 with both correctly and inversely oriented insertions of the MuST transposon could grow in the presence of Cm as all genetic components necessary for displaying CmR were contained in this engineered transposon as described earlier.

Materials and Methods
Materials.

A Mu transposon containing the chloramphenicol resistance (CmR) gene and MuA transposase were purchased from Dharmacon products (Lafayette, Colo., USA). Bioassay dishes were purchased from Thermo Fisher scientific (Rochester, N.Y., USA). High fidelity platinum Pfx DNA polymerase and DH5α cells were purchased from Life technologies (Carlsbad, Calif., USA). All DNA purification kits and columns were purchased from Zymo Research Corporation (Irvine, Calif., USA). Methyltransferase deficient (dam−/dcm−) competent E. coli cells, the PUC19 plasmid, restriction enzymes and T4 DNA ligase were purchased from New England Biolabs, Inc. (Ipswich, Mass., USA).

PCR for Construction of the MuST Transposon.

BclI and AgeI sites were genetically appended to the wild-type Mu transposon using PCR with forward (5'-TGATCAG-

TABLE 1

Nucleotide sequences of bcx inserted into PUC19 obtained from ten randomly selected library members
(SEQ ID NOS 1-20, respectively, in order of appearance)

| | Correctly oriented insertion | |
|---|---|---|
| 212 | c g c a c *TGATCA* A G C C . . . T G G *ACCGGT TCA* c g c a c a | 207 |
| 215 | a c a g a *TGATCA* A G C C . . . T G G *ACCGGT TCA* a c a g a t | 210 |
| 329 | g g g g a *TGATCA* A G C C . . . T G G *ACCGGT TCA* g g g g a t | 324 |
| 489 | c t g t g *TGATCA* A G C C . . . T G G *ACCGGT TCA* c t g t g t | 484 |
| 556 | c t g g g *TGATCA* A G C C . . . T G G *ACCGGT TCA* c t g g g g | 551 |
| | Inversely oriented insertion | |
| 96 | a g c c c *TGATCA* A G C C . . . T G G *ACCGGT TCA* a g c c c g | 101 |
| 184 | c a t a t *TGATCA* A G C C . . . T G G *ACCGGT TCA* c a t a t g | 189 |
| 247 | c c a t t *TGATCA* A G C C . . . T G G *ACCGGT TCA* c c a t t c | 252 |
| 281 | c g g t g *TGATCA* A G C C . . . T G G *ACCGGT TCA* c g g t g c | 286 |
| 419 | c t g t g *TGATCA* A G C C . . . T G G *ACCGGT TCA* c t g t g t | 424 |

The lowercase letters represent nucleotide sequences derived from PUC19.
The plain uppercase letters indicate the first and last codons of bcx.
The bold italic uppercase letters represent BClI(TGATCA) + A or AgeI(ACCGGT) + TCA.
The numbers represent position of the first and last nucleotides indicated according to the PUC19 plasmid map shown in FIG. 5.

The sequencing results also demonstrated that (1) the bcx gene was intact after random insertion into PUC19 (data not shown) and (2) 5 bp precise duplication of the PUC19 sequence occurred upon random insertion of bcx as expected (Table 1). The implication is that inter-domain linkers, Xaa-Asp-Gln and Thr-Gly-Ser were connected in-frame to BCX (FIG. 1B and Table 1). These results demonstrate that optimal control of inter-domain linker residues was possible during construction of random insertion libraries using our method.

GCGCACGAAAAACGCGAA-3' (SEQ ID NO: 21)) and reverse (5'-TGCGAAAGCGCAAAAAGCACGTGGC-CAAGT-3' (SEQ ID NO: 22)) primers. For PCR amplification of the MuST transposon, 5'-TGTGAAATACCGCACA-GATGATCA-3' (SEQ ID NO: 23) and 5'-TGGCCAAGTTGTCTACGCA-3' (SEQ ID NO: 24) were used as forward and reverse primers, respectively. All PCR reactions were carried out with platinum Pfx DNA polymerase.

Random Insertion of the Mu Transposon and the MuST Transposon into PUC19.

The transposition reaction was carried out with 20 ng of the Mu transposon, 160 ng of the target DNA (i.e., PUC19) and 22 ng of MuA transposase in 1× reaction buffer (25 mM Tris HCl, 10 mM MgCl2, 0.05% Triton X-100 and 10% glycerol at pH 8.0) in a total volume of 20 μl at 30° C. Transposition of the MuST transposon into PUC19 was performed similarly. The transposition reaction mixtures were incubated for 1 hour at 30° C. MuA transposase was then heat-inactivated at 75° C. for 15 minutes to stop the transposition reaction. Aliquots (0.5 μl) of transposition reaction mixtures were subsequently transformed into 50 μl of DH5α by electroporation at 1700 V using a Bio-Rad Gene Pulser (Hercules, Calif., USA). The electroporated cells were then incubated in SOC media at 37° C. for 1 hour with constant shaking at 250 rpm in a New Brunswick Scientific Innova TM4230 incubator (Edison, N.J., USA).

Five % of recovered cells were plated on small LB-agar plates supplemented with 50 μg/ml of chloramphenicol (Cm) and 100 μg/ml of ampicillin (Amp). Colonies grown on these plates during overnight incubation at 37° C. were counted to calculate a transposition efficiency (i.e., the number of colonies grown on the Amp/Cm plates after transformation with 0.5 μl of the transposition mixture). Note that the CmR gene was included in the Mu transposon and the MuST transposon, but not the wild-type PUC19 plasmid which contained the AmpR gene. As such, only colonies harboring PUC19 with the inserted Mu transposon or MuST transposon were able to grow on Amp/Cm plates. Another 5% of recovered cells were plated on small LB-agar plates supplemented with 100 μg/ml of Amp to calculate a transformation efficiency (i.e., the number of colonies grown on the Amp plates after transformation with 0.5 μl of the transposition mixture). As PUC19 contains the AmpR gene, all transformants (i.e., those harboring PUC19 with and without the inserted transposon) were able to grow on Amp plates. The recovered cells were also plated on large Amp/Cm plates, followed by overnight incubation at 37° C. Colonies grown on these plates were then collected by adding 4×15 ml storage media (36 ml of LB, 18 ml of 50% glycerol and 6 ml of 20% (w/v) glucose) to the top of the each plate followed by the transfer of cells from media into polypropylene centrifuge tubes. The cell suspensions were subsequently centrifuged at 5000 rpm at 4° C. for 10 minutes and supernatants were then decanted. The plasmids with the randomly inserted transposons were then extracted en masse using the Zymo plasmid midiprep kit.

Preparation of the Linear PUC19 Plasmids with Random Single Cuts by Removal of the Inserted MuST Transposons.

The PUC19 plasmids with the randomly inserted MuST transposons extracted from DH5α were subsequently transformed into dam−/dcm− competent E. coli cells using heat shock to prepare the plasmids free of Dam methylation. Heat shock at 42° C. was provided for 30 seconds after incubating DNA-cell mixtures on ice for 30 minutes. The cells were placed on ice for 5 minutes after heat shock and subsequently incubated at 37° C. with constant shaking at 250 rpm for 1 hour. The Dam methylation-free PUC19 plasmids with the randomly inserted MuST transposons were double digested by BclI and AgeI restriction enzymes to remove the MuST transposon sequence and to create sticky-ends for subsequent ligation with bcx. The resulting PUC19 plasmids with random single cuts were purified en masse using the Zymo research gel extraction kit.

Sticky-End Ligation of bcx into Random Single Cut PUC19 Plasmids.

The bcx gene with BclI and AgeI restriction enzyme sites appended at 5' and 3' ends, respectively, was genetically constructed by PCR. The PCR product was then purified by the Zymo research gel extraction kit, followed by double digestion with BclI and AgeI restriction enzymes to generate sticky-ends. After purification, the digested bcx gene was ligated with the random single cut PUC19 plasmids using T4 ligase. The ligation mixture was purified by ethanol precipitation and subsequently transformed into DH5α by electroporation at 2000 V using a Bio-Rad Gene Pulser. The electroporated cells were then incubated in SOC media at 37° C. for 1 hour with constant shaking at 250 rpm in a New Brunswick Scientific Innova TM4230 incubator. The electroporated cells were subsequently plated on LB-agar plates supplemented with 100 μg/ml of Amp and incubated for 16-24 hour at 37° C. Selected colonies were re-grown and the plasmids were subsequently extracted using the Zymo plasmid miniprep kits for sequencing at Genewiz, Inc. (South Plainfield, N.J., USA).

For insertional fusion, a combinatorial approach has proven to be effective to couple functionalities of two protein domains in such a way that is difficult to predict by rational design. Random insertion which has been facilitated many purposes like, to regulate biological functions by designed molecular switches are advantageous and capable for a numerous applications which include the creation of biosensor modulators of gene transcription and cell signaling pathways, novel biomaterials and many others. Construction of a random protein domain insertion library is a pre-requisite for comprehensive and extensive evaluation of various mode of insertional fusion. Inter-domain linker residues may also affect the outcome of insertional fusion and should thus be optimized to increase a likelihood of functional insertion.

The invention may be used in both academic and research institutions in life science technologies to develop new chimeric proteins with multiple intimately interacting domains and coupled functionalities. The transposon provides an extension in the pool of techniques already available. The MuST transposon and the technique used to generate it are easy to use and execute, thus providing an advantage in the development of products. It utilizes some of the most commonly used recombinant DNA/protein techniques such as polymerase chain reaction and sticky end ligation in a systematic, controlled manner that greatly improves library efficiency. The uniquely designed transposon which generates short sequence linkers is specially suited to random insertion of entire domains of one protein into another with optimal linker length, an attribute useful in the design of proteins with cross-talking, combined functional capabilities. At present many transposons allow for the generation of multi-domain proteins, but these proteins many times are limited by spatial proximity, where domain interaction is inherently limited by the long linkers associated with the transposon.

In contrast to the present kits offered on the market that utilize transposon technologies (EZ-Tn5™, and other EZ-Tn kits from Epicenter, Gene Jumper oriV Transposon Kit from Invitrogen Corp, Piggy Bac transposon system from System Biosciences as well as Sleeping Beauty to name a few), the MuST transposon with its designed inter domain linker sequence allows for more efficient interaction between domains thereby allowing for improvements in characteristics such as stability and allostery. Therapeutic applications such as Gene therapy (and the aforementioned examples), already aided by transposition will be another beneficiary from a proposed technology such as the MuST transposon since the MuST transposons provides a more intimate crosstalking and sharing of different characteristics of desired enzymes or proteins. A technology such as the MuST transposon can be very efficient in the generation of multifunctional protein libraries as potential services such as library generation can be offered by new and existing companies or an easy to use kit from which even the novice researcher can use. In industrial settings and to a lesser extent, academic settings, cost advantage presents itself in the form of labor savings as high level skill is not needed to carry out the transposition. The reduced number of steps (naive libraries can be generated within a couple of days or even hours) is advantageous in that it helps to reduce both the cost of labor (lower skilled employees may be used) and other labor associated cost (reduced time for library generation, work hours etc.).

By considering the above mentioned importance, our described engineered transposon-based method is a novel and important molecular tool for facile construction of a random protein domain insertion library with optimal control of interdomain linker residues through sticky-end rather than blunt-end ligation between host and guest DNAs. Our method can also be applied for construction of a wide range of protein insertion complexes. Due to such novel yet significant scientific implications, we strongly believe that our invention should be highly interesting for the commercialization purpose to make random fusion libraries.

It will be appreciated by persons of ordinary skill in the art that the present invention is not limited by what has been particularly shown and described herein above. Rather, the foregoing detailed description of the preferred embodiments and the appended figures have been presented only for illustrative and descriptive purposes. They are not intended to be exhaustive and are not intended to limit the scope and spirit of the invention. The embodiments were selected and described to best explain the principles of the invention and its practical applications. One skilled in the art will recognize that many variations can be made to the invention disclosed in this specification without departing from the scope and spirit of the invention.

REFERENCES

[1] H. Bach, Y. Mazor, S. Shaky, A. Shoham-Lev, Y. Berdichevsky, D. L. Gutnick, I. Benhar, *Escherichia coli* maltose-binding protein as a molecular chaperone for recombinant intracellular cytoplasmic single-chain antibodies, J. Mol. Biol. 312 (2001) 79-93.

[2] L. M. Bergeron, L. Gomez, T. A. Whitehead, D. S. Clark, Self-renaturing enzymes: design of an enzyme-chaperone chimera as a new approach to enzyme stabilization, Biotechnol. Bioeng. 102 (2009) 1316-1322.

[3] W. R. Edwards, K. Busse, R. K. Allemann, D. D. Jones, Linking the functions of unrelated proteins using a novel directed evolution domain insertion method, Nucleic Acids Res. 36 (2008) e78.

[4] G. S. Baird, D. A. Zacharias, R. Y. Tsien, Circular permutation and receptor insertion within green fluorescent proteins, Proc. Natl. Acad. Sci. USA 96 (1999) 11241-11246.

[5] M. Ostermeier, Engineering allosteric protein switches by domain insertion, Protein Eng. Des. Sel. 18 (2005) 359-364.

[6] B. Pierre, T. Xiong, L. Hayles, V. R. Guntaka, J. R. Kim, Stability of a guest protein depends on stability of a host protein in insertional fusion, Biotechnol. Bioeng. 108 (2011) 1011-1020.

[7] J. Li, I. Gierach, A. R. Gillies, C. D. Warden, D. W. Wood, Engineering and optimization of an allosteric biosensor protein for peroxisome proliferator-activated receptor gamma ligands, Biosens. Bioelectron. 29 (2011) 132-139.

[8] C. S. Kim, B. Pierre, M. Ostermeier, L. L. Looger, J. R. Kim, Enzyme stabilization by domain insertion into a thermophilic protein, Protein Eng. Des. Sel. 22 (2009) 615-623.

[9] L. Jin, B. Baker, R. Mealer, L. Cohen, V. Pieribone, A. Pralle, T. Hughes, Random insertion of split-cans of the fluorescent protein venus into Shaker channels yields voltage sensitive probes with improved membrane localization in mammalian cells, J. Neurosci. Methods 199 (2011) 1-9.

[10] M. M. Krishna, S. W. Englander, The N-terminal to C-terminal motif in protein folding and function, Proc. Natl. Acad. Sci. USA. 102 (2005) 1053-1058.

[11] T. A. Cutler, B. M. Mills, D. J. Lubin, L. T. Chong, S. N. Loh, Effect of interdomain linker length on an antagonistic folding-unfolding equilibrium between two protein domains, J. Mol. Biol. 386 (2009) 854-868.

[12] J. X. Feliu, A. Villaverde, Engineering of solvent-exposed loops in *Escherichia coli* beta-galactosidase, FEBS Lett. 434 (1998) 23-27.

[13] Y. Li, A. M. Sierra, H. W. Ai, R. E. Campbell, Identification of sites within a monomeric red fluorescent protein that tolerate peptide insertion and testing of corresponding circular permutations, Photochem. Photobiol. 84 (2008) 111-119.

[14] M. Berrondo, M. Ostermeier, J. J. Gray, Structure prediction of domain insertion proteins from structures of individual domains, Structure 16 (2008) 513-527.

[15] A. D. Schuyler, H. A. Carlson, E. L. Feldman, Computational methods for predicting sites of functionally important dynamics, J. Phys. Chem. B 113 (2009) 6613-6622.

[16] C. M. Wright, R. C. Wright, J. R. Eshleman, M. Ostermeier, A protein therapeutic modality founded on molecular regulation, Proc. Natl. Acad. Sci. USA 108 (2011) 16206-16211.

[17] R. M. Biondi, P. J. Baehler, C. D. Reymond, M. Veron, Random insertion of GFP into the cAMP-dependent protein kinase regulatory subunit from Dictyostelium discoideum, Nucleic Acids Res. 26 (1998) 4946-4952.

[18] R. S. Gokhale, C. Khosla, Role of linkers in communication between protein modules, Curr. Opin. Chem. Biol. 4 (2000) 22-27.

[19] W. Wriggers, S. Chakravarty, P. A. Jennings, Control of protein functional dynamics by peptide linkers, Biopolymers 80 (2005) 736-746.

[20] R. A. George, J. Heringa, An analysis of protein domain linkers: their classification and role in protein folding, Protein Eng. 15 (2002) 871-879.

[21] C. R. Robinson, R. T. Sauer, Optimizing the stability of single-chain proteins by linker length and composition mutagenesis, Proc. Natl. Acad. Sci. USA 95 (1998) 5929-5934.

[22] P. Argos, An investigation of oligopeptides linking domains in protein tertiary structures and possible candidates for general gene fusion, J. Mol. Biol. 211 (1990) 943-958.

[23] S. Hayward, Structural principles governing domain motions in proteins, Proteins 36 (1999) 425-435.

[24] J. M. Betton, J. P. Jacob, M. Hofnung, J. K. Broome-Smith, Creating a bifunctional protein by insertion of beta-lactamase into the maltodextrin-binding protein, Nat. Biotechnol. 15 (1997) 1276-1279.

[25] G. Guntas, T. J. Mansell, J. R. Kim, M. Ostermeier, Directed evolution of protein switches and their applica-

[26] J. Tullman, G. Guntas, M. Dumont, M. Ostermeier, Protein switches identified from diverse insertion libraries created using S1 nuclease digestion of supercoiled-form plasmid DNA, Biotechnol. Bioeng. 108 (2011) 2535-2543.

[27] G. Guntas, M. Ostermeier, Creation of an allosteric enzyme by domain insertion, J. Mol. Biol. 336 (2004) 263-273.

[28] H. Murakami, T. Hohsaka, M. Sisido, Random insertion and deletion of arbitrary number of bases for codon-based random mutation of DNAs, Nat. Biotechnol. 20 (2002) 76-81.

[29] S. Haapa, S. Taira, E. Heikkinen, H. Savilahti, An efficient and accurate integration of mini-Mu transposons in vitro: a general methodology for functional genetic analysis and molecular biology applications, Nucleic Acids Res. 27 (1999) 2777-2784.

[30] W. S. Reznikoff, Tn5 transposition: a molecular tool for studying protein structure-function, Biochem. Soc. Trans. 34 (2006) 320-323.

[31] K. Mizuuchi, Transpositional recombination: mechanistic insights from studies of mu and other elements, Annu. Rev. Biochem. 61 (1992) 1011-1051.

[32] G. Chaconas, Studies on a "jumping gene machine": higher-order nucleoprotein complexes in Mu DNA transposition, Biochem. Cell Biol. 77 (1999) 487-491.

[33] T. A. Baker, E. Kremenstova, L. Luo, Complete transposition requires four active monomers in the mu transposase tetramer, Genes Dev. 8 (1994) 2416-2428.

[34] I. Goldhaber-Gordon, T. L. Williams, T. A. Baker, DNA recognition sites activate MuA transposase to perform transposition of non-Mu DNA, J. Biol. Chem. 277 (2002) 7694-7702.

[35] I. Goldhaber-Gordon, M. H. Early, T. A. Baker, The terminal nucleotide of the Mu genome controls catalysis of DNA strand transfer, Proc. Natl. Acad. Sci. USA 100 (2003) 7509-7514.

[36] N. L. Craig, Unity in transposition reactions, Science 270 (1995) 253-254.

[37] K. Mizuuchi, Transpositional recombination: mechanistic insights from studies of mu and other elements, Annu. Rev. Biochem. 61 (1992) 1011-1051.

[38] R. Mealer, H. Butler, T. Hughes, Functional fusion proteins by random transposon-based GFP insertion, Methods Cell Biol. 85 (2008) 23-44.

[39] J. A. Gregory, E. G. Becker, J. Jung, I. Tuwatananurak, K. Pogliano, Transposon assisted gene insertion technology (TAGIT): a tool for generating fluorescent fusion proteins, PLoS One 5 (2010) e8731.

[40] M. Osawa, H. P. Erickson, Probing the domain structure of FtsZ by random truncation and insertion of GFP, Microbiology 151 (2005) 4033-4043.

[41] V. Sgaramella, S. D. Ehrlich, Use of the T4 polynucleotide ligase in the joining of flush-ended DNA segments generated by restriction endonucleases, Eur. J. Biochem. 86 (1978) 531-537.

[42] A. H. Lund, M. Duch, F. S. Pedersen, Increased cloning efficiency by temperature-cycle ligation, Nucleic Acids Res. 24 (1996) 800-801.

[43] E. Loukianov, T. Loukianova, M. Periasamy, Efficient cloning method that selects the recombinant clones, Biotechniques 23 (1997) 292-295.

[44] I. Goldhaber-Gordon, M. H. Early, T. A. Baker, MuA transposase separates DNA sequence recognition from catalysis, Biochemistry 42 (2003) 14633-14642.

[45] G. E. Geier, P. Modrich, Recognition sequence of the dam methylase of *Escherichia coli* K12 and mode of cleavage of Dpn I endonuclease, J. Biol. Chem. 254 (1979) 1408-1413.

---

What is claimed is:

1. A method for facile construction of a random domain insertion library comprising the steps of:
 providing an engineered transposon;
 randomly transposing the engineered transposon into a host DNA sequence, using plasmid PUC19 containing lacZα as the host DNA sequence;
 employing sticky-end ligation between the host DNA sequence and a guest DNA sequence, using a gene coding for xylanase from *bacillus circulans* (BCX) as the guest DNA sequence; and
 removing the engineered transposon from the host DNA sequence by restriction enzyme digestion, wherein the restriction enzyme digestion is double digestion using BclI and AgeI restriction enzymes,
 thereby generating a plasmid for the domain insertion library.

2. The method as claimed in claim 1, wherein the engineered transposon is a Mu transposon randomly transposed into the host DNA sequence in vitro.

3. The method as claimed in claim 1, further comprising the step of sticky-end ligating random single cut plasmids resulting from the restriction enzyme digestion with the guest DNA sequence.

4. The method as claimed in claim 2, wherein the random transposition of the Mu transposon into the host DNA sequence occurs in the presence of MuA transposase.

5. A method for facile construction of a random domain insertion library comprising the steps of:
 providing an engineered transposon, wherein the engineered transposon is a Mu transposon;
 mutating the Mu transposon to introduce a BclI site (TGATCA) and an AgeI site (ACCGGT) at 5' and 3' ends of the Mu transposon, respectively;
 randomly transposing the transposon into a host DNA sequence, using plasmid PUC19 containing lacZα as the host DNA sequence, wherein the Mu transposon is randomly transposed into the host DNA sequence in vitro, wherein the random transposition of the Mu transposon into the host DNA sequence occurs in the presence of MuA transposase; and
 employing sticky-end ligation between the host DNA sequence and a guest DNA sequence, using a gene coding for xylanase from *bacillus circulans* (BCX) as the guest DNA sequence.

6. The method as claimed in claim 5, wherein the resulting engineered Mu transposon contains an additional 18 bp fragment upstream of the BclI site and an additional 10 bp fragment downstream of the AgeI site.

7. The method as claimed in claim 5, further comprising, to minimize undesired effects on transposition, making most mutations to create the engineered transposon outside of Mu transposon regions involved in various transposition, and making no mutation in transposon cleavage sites.

8. The method as claimed in claim 7, further comprising placing the BclI site+A (TGATCAA) in a second reading frame where GATCAA encodes for Asp-Gln as inter-domain linker residues fused to an N-terminus of the guest DNA sequence, and placing the AgeI site+TCA (ACCGGTTCA) in a first frame where ACCGGTTCA encodes Thr-Gly-Ser as inter-domain linker residues fused to a C terminus of the guest DNA sequence.

9. A method for facile construction of a random domain insertion library comprising the steps of:
 providing an engineered Mu transposon;
 randomly transposing the engineered transposon into a host DNA sequence in vitro and in the presence of MuA transposase;
 removing the engineered transposon from the host DNA sequence by restriction enzyme digestion, wherein the restriction enzyme digestion is double digestion using BclI and AgeI restriction enzymes; and
 sticky-end ligating random single cut plasmids resulting from the restriction enzyme digestion with a guest DNA sequence,
 thereby generating a plasmid for the domain insertion library.

10. The method as claimed in claim 9, wherein the guest DNA sequence is a gene coding for xylanase from *bacillus circulans* (BCX) and the host DNA sequence is a plasmid PUC19 containing lacZα.

11. The method as claimed in claim 9, further comprising mutating the Mu transposon to introduce a BclI site (TGATCA) and an AgeI site (ACCGGT) at 5' and 3' ends of the Mu transposon, respectively.

12. The method as claimed in claim 11, further comprising, to minimize undesired effects on transposition, making most mutations to create the engineered transposon outside of Mu transposon regions involved in various transposition, and making no mutation in transposon cleavage sites.

13. The method as claimed in claim 12, further comprising placing the BclI site+A (TGATCAA) in a second reading frame where GATCAA encodes for Asp-Gln as inter-domain linker residues fused to an N-terminus of the guest DNA sequence, and placing the AgeI site+TCA (ACCGGTTCA) in a first frame where ACCGGTTCA encodes Thr-Gly-Ser as inter-domain linker residues fused to a C terminus of the guest DNA sequence.

14. The method as claimed in claim 12, wherein the engineered Mu transposon contains an additional 18 bp fragment upstream of the BclI site and an additional 10 bp fragment downstream of the AgeI site.

* * * * *